US00PP36246P3

(12) United States Plant Patent
Nishikawa

(10) Patent No.: US PP36,246 P3
(45) Date of Patent: Nov. 5, 2024

(54) ***DELOSPERMA* PLANT NAMED 'S3red'**

(50) Latin Name: *Delosperma nubigenum*
Varietal Denomination: S3red

(71) Applicant: Koichiro Nishikawa, Okayama (JP)

(72) Inventor: Koichiro Nishikawa, Okayama (JP)

( * ) Notice: Subject to any disclaimer, the term of this patent is extended or adjusted under 35 U.S.C. 154(b) by 0 days.

(21) Appl. No.: 18/441,197

(22) Filed: Feb. 14, 2024

(65) Prior Publication Data

US 2024/0341211 P1 Oct. 10, 2024

(30) Foreign Application Priority Data

Apr. 6, 2023 (QZ) ..... PBR 2023/0831

(51) Int. Cl.
*A01H 5/02* (2018.01)
*A01H 6/00* (2018.01)

(52) U.S. Cl.
USPC ..... Plt./422

(58) Field of Classification Search
USPC ..... Plt./422
CPC ..... A01H 5/02; A01H 5/00; A01H 6/00
See application file for complete search history.

(56) References Cited

U.S. PATENT DOCUMENTS

PP25,572 P2 * 5/2015 Nishikawa ..... A01H 5/02
Plt./422

* cited by examiner

*Primary Examiner* — June Hwu
(74) *Attorney, Agent, or Firm* — Penny J. Aguirre

(57) ABSTRACT

A new cultivar of *Delosperma* plant named 'S3red' that is characterized by its flowers with petals that are magenta pink on the outer region and white towards the center of the flower surrounding yellow-white petaloids, its short internodes and an abundance of flowering side branches, its neat, naturally rounded plant shape with suitability for growing in small containers, its very floriferous and long blooming habit; blooming from early summer into autumn, its very floriferous and long blooming habit; blooming from early summer into autumn, its very high flower quantity, forming a flower carpet when in full bloom, its ease of growing with no need for vernalization, and its high tolerance to heat, drought, and humidity.

2 Drawing Sheets

Botanical classification: *Delosperma nubigenum.*
Variety denomination: 'S3red'.

CROSS-REFERENCE A RELATED APPLICATIONS

This application claims priority to European Community Plant Variety Office (CPVO) Plant Breeder's Rights Application No. 2023/0831 filed on Apr. 6, 2023, under 35 U.S.C. 119(f), the entire contents of which is incorporated by reference herein. The Applicant received the information for the Plant breeders' rights application directly from the Inventor. This application is co-pending with U.S. Plant Patent Applications filed for plants derived from the same breeding program that are entitled *Delosperma* Plant Named 'S3ora' (U.S. Plant patent application Ser. No. 18/441, 147), *Delosperma* Plant Named 'S3ros' (U.S. Plant patent application Ser. No. 18/441,246), *Delosperma* 'Plant Named 'S3whi' (U.S. Plant patent application Ser. No. 18/441,346), and *Delosperma* 'Plant Named 'S3yel' (U.S. Plant patent application Ser. No. 18/441,055).

BACKGROUND OF THE INVENTION

The present invention relates to a new and distinct cultivar of *Delosperma* plant, botanically known as *Delosperma nubigenum* 'S3red' and will be referred to hereinafter by its cultivar name, 'S3red'. The new cultivar of *Delosperma* is an evergreen perennial grown for container and landscape use.

The new cultivar was derived from a controlled breeding program conducted by the Inventor in Katsuta-Gun, Okayama-Pref., Japan. The overall purpose of the breeding program was to develop new cultivars of *Delosperma* plants with short stem internodes, good branching with dense growth habits, neat growing habits with suitability for growing in small containers, and very high flower counts.

'S3red' was selected in the Inventor's trial garden in October of 2019 as a single unique plant from amongst the seedlings derived from crosses made in 2016 between unnamed and unpatented plants from the Inventor's breeding program. Seeds were pooled from the crosses and therefore the exact parentage is unknown.

Asexual propagation of the new cultivar was first accomplished by stem cuttings in October of 2019 by the Inventor in Katsuta-Gun, Okayama-Pref., Japan. Asexual propagation by stem cuttings has determined the characteristics of the new cultivar are stable and reproduced true to type in successive generations.

SUMMARY OF THE INVENTION

The following traits have been repeatedly observed and are determined to be the characteristics of the new cultivar. These attributes in combination distinguish 'S3red' as a unique cultivar of *Delosperma.*

1. 'S3red' exhibits flowers with petals that are magenta pink on the outer region and white towards the center of the flower surrounding yellow-white petaloids.
2. 'S3red' exhibits a very compact, densely branched, and low growing plant habit.
3. 'S3red' exhibits small internodes and an abundance of flowering side branches.
4. 'S3red' exhibits a neat, naturally rounded plant shape with suitability for growing in small containers.
5. 'S3red' exhibits a very floriferous and long blooming habit; blooming from early summer into autumn.
6 'S3red' exhibits a very high flower quantity, forming a flower carpet when in full bloom.
7. 'S3red' exhibits ease of growing with no need for vernalization.
8. 'S3red' exhibits a high tolerance to heat, drought, and humidity.

'S3red' can be most closely compared to the *Delosperma* cultivars 'WOWDOY3' (U.S. Plant Pat. No. 25,600) and 'WOWDAY2' (U.S. Plant Pat. No. 25,645). 'WOWDOY3' is similar to 'S3red' in having a floriferous habit and in being the same species. 'WOWDOY3' differs from 'S3red' in having longer internodes, less suitability for use in small containers, and flower petals that are orange on the outer region. 'WOWDAY2' is similar to 'S3red' in having a floriferous habit, flower petals that are red on the outer region and yellow towards the center, and in being the same species. 'WOWDAY2' differs from 'S3red' in having less suitability for use in small containers, flowers that are larger in size, and longer internodes.

'S3red' can also be compared to co-pending cultivars of *Delosperma nubigenum*. They are all similar to 'S3red' in plant habit in having short internodes and suitability for growing in small containers. 'S3ora' differs from 'S3red' in having flowers with petals that are orange on the outer region and yellow towards the center of the flower surrounding yellow petaloids. 'S3ros' differs from 'S3red' in having flowers with petals that are violet on the outer region and white towards the center of the flower surrounding white petaloids. 'S3whi' differs from 'S3red' in having flowers with petals that are white surrounding white-yellow petaloid. 'S3yel' differs from 'S3red' in having flowers with yellow petals and yellow petaloids.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to website listings by Plantipp, Kientzler Jungpflanzen, FlorSAIKA, Darwin Perennials, Globe Planter, Express Seed Company, LinkedIn, Facebook, Matteo Ragni, and Gustav Schlüter.

BRIEF DESCRIPTION OF THE DRAWINGS

The accompanying color photographs illustrate the overall appearance and distinct characteristics of the new *Delosperma*. The photographs were taken of 3-month-old plants of the new cultivar as grown outdoors in 12-cm pots in Gensingen, Germany.

The photograph in FIG. 1 provides a top view of 'S3red' in bloom.

Figure 1:
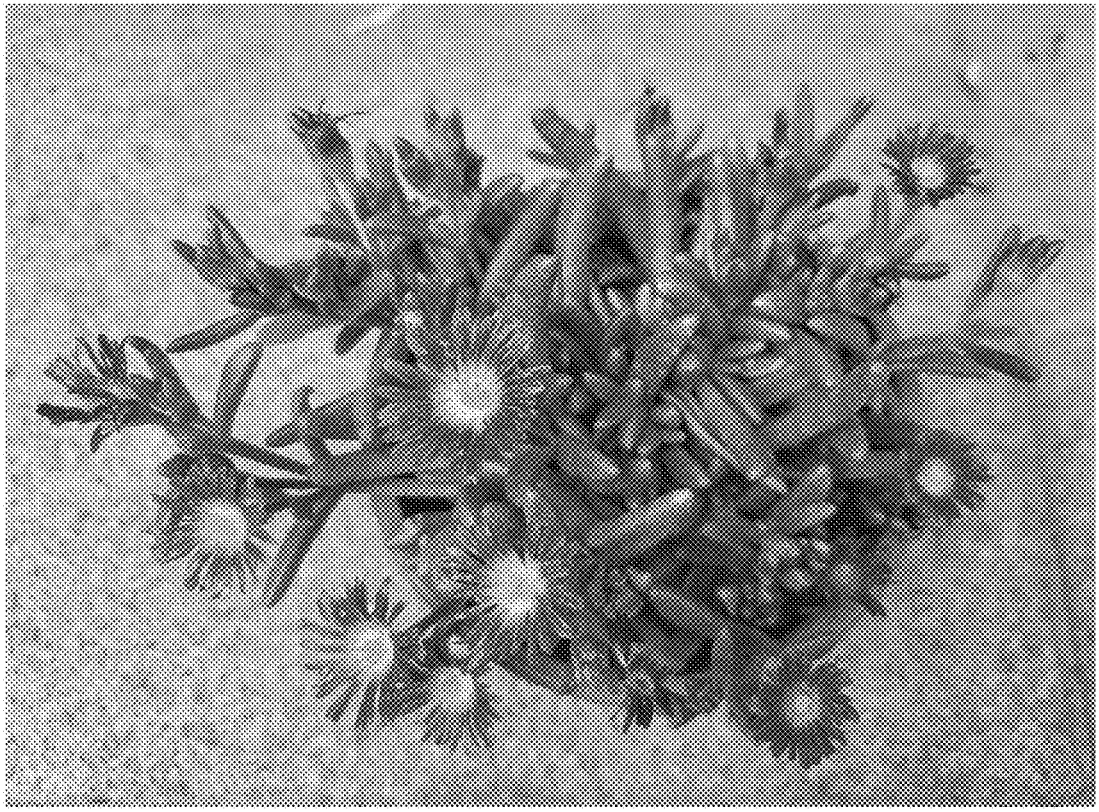
Figure 2:
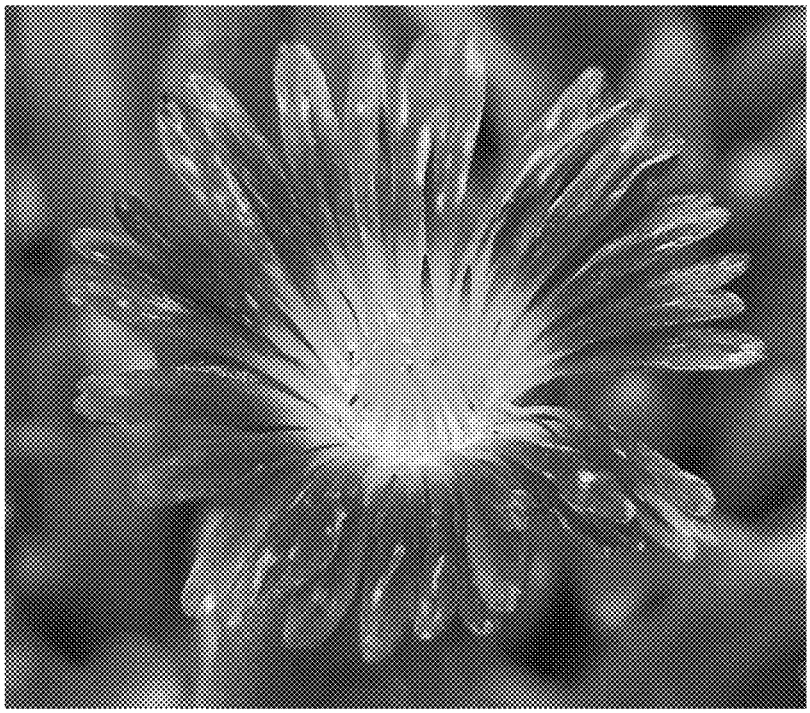

The photograph in FIG. 2 provides a close-up view of a flower of 'S3red'.

Figure 3:
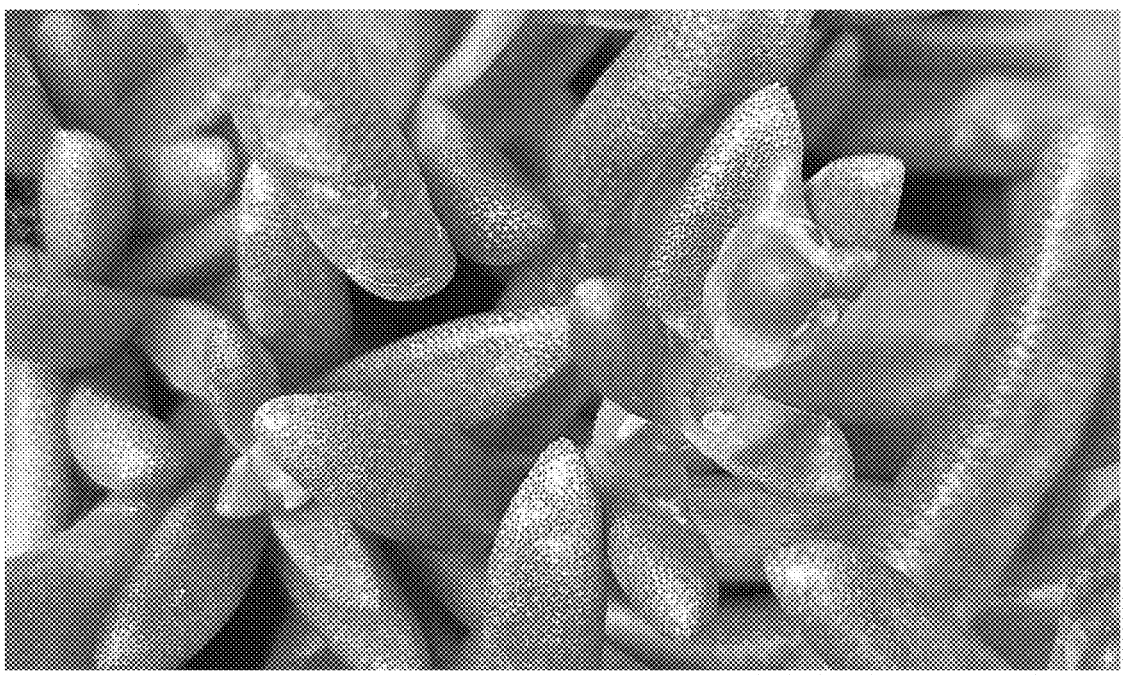

The photograph in FIG. 3 provides a close-up view of the foliage of 'S3red'.

The colors in the photographs are as close as possible with the digital photography and printing techniques utilized and the color codes in the detailed botanical description accurately describe the new *Delosperma*.

DETAILED BOTANICAL DESCRIPTION

The following is a detailed description of 3-month-old plants of the new cultivar as grown outdoors in 12-cm pots in Gensingen, Germany. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Blooms from early summer into autumn in The Netherlands.

*Plant type*.—Evergreen perennial.

*Plant habit*.—Flattened, dense, rounded.

*Height and spread*.—Reaches an average of 9 cm in height, 19 cm in width as a 3-month-old plant grown in a container.

*Cold hardiness*.—Observed to be hardy to at least U.S.D.A. Zone 7.

*Diseases and pests*.—No susceptibility or resistance to diseases or pests has been observed.

*Root description*.—Fibrous roots, primarily 161D in color.

*Propagation*.—Stem cuttings.

*Root development*.—8 weeks for root initiation, 4 months from a plug to young plant in a P9 container.

*Growth habit*.—Moderate.

Stem description:

*Shape*.—Round.

*Stem color*.—Main stems young and mature; N199D and 164B, secondary stems; 144B to 144C, flushed with 180B.

*Stem size*.—Lateral branches; an average of 12 cm in length and 4 mm in diameter.

*Internode length*.—An average of 2.3 cm.

*Stem substance*.—Succulent.

*Stem surface*.—Moderately glossy, moderately pubescent with very short glandular hairs; an average of 0.2 mm in length and closest to 155C in color.

*Branching habit*.—Densely branched, 5 to 7 secondary branches per main branch, 8 tertiary branches per secondary branch.

Foliage description:

*Leaf shape*.—Ligulate.

*Leaf substance*.—Succulent.

*Leaf division*.—Simple.

*Leaf base*. Cuneate.

*Leaf apex*.—Acute.

*Leaf venation*.—No veins visible.

*Leaf margins*.—Entire.

*Leaf arrangement*.—Opposite.

*Leaf surface* (*upper and lower surface*).—Slightly glossy, slightly pubescent with very short glandular hairs; an average of 0.2 mm in length, matches surface color.

*Leaf color*.—137B, occasionally with 180C.

*Leaf size*.—Up to 5.5 cm in length and 7 mm in width.

*Leaf quantity*.—10 to 12 per lateral branch.

*Leaf attachment*.—Sessile.

Inflorescence description:

*Inflorescence type*.—Flowers solitary, terminal.

*Flower number*.—An average of 1 per lateral stem.

*Flower fragrance*.—None.

*Flower aspect*.—Slightly outward to upright.

*Flower longevity*.—A few days, self-cleaning.

*Flower type*.—Single.

*Flower size*.—Average of 2.1 cm in diameter and 1 cm in depth.

*Flower buds*.—Broadly ovate to oblong in shape, an average of 7 mm in length, 5 mm in diameter, color; 61A, surface is smooth.

*Calyx*.—Rotate in shape, average of 7 mm in depth and 1.4 cm in diameter.

*Sepals*.—5, rotate, ovate in shape, margin entire, an average of 7 mm in length and 3 mm in width, broadly acute apex, broadly cuneate base, surface is smooth and dull, color young and mature upper and lower surface; 137C and 144C.

*Petals*.—An average of 46 per flower, rotate and slightly curved downward, oblanceolate in shape, surface is moderately glossy on both surfaces, margin entire, apex obtuse, base cuneate, an average of 1.1 cm in length and 2 mm in width, color: opening and fully open upper surface 61A and 60A, center 13A and base NN155D, opening and fully open lower surface NN74A, a hint of 13A.

*Petaloids*.—An average of 18 per flower, rotate and near vertical surrounding stamens, lanceolate in shape, moderately to highly glossy on both surfaces, margin entire, apex obtuse, base truncate, an average of 5 mm in length and 1 mm in width, color: both surfaces ranging between 13A and base NN155D with sporadic tips 60A.

*Peduncle*.—Average of 1.3 cm in length and 2 mm in diameter, straight on top of lateral branch at 0°, 145A and 173A in color, surface moderately glossy, sparsely to moderately pubescent with very short glandular hairs.

*Pedicel*.—None.

Reproductive organs:

*Pistils*.—5, an average of 2 mm in length, stigma; triangular shaped, style and stigma; (not distinguishable) combined an average of 2 mm in length, NN155D and 9B in color, ovary; 4 mm in length and width, 144C in color.

*Stamens*.—Average of 60, anthers; dorsifixed and narrowly oblong in shape, an average of 0.5 mm in diameter, 6A in color, filaments; 4 mm in length, color; NN155D, top 8A, pollen; moderate to high in quantity and 6A in color.

*Fruit*.—Fruit and seed production was not observed under the conditions tested.

It is claimed:

1. A new and distinct variety of *Delosperma* plant named 'S3red' as described and illustrated herein.

* * * * *